United States Patent [19]

Leftheris et al.

[11] Patent Number: 4,953,973
[45] Date of Patent: Sep. 4, 1990

[54] DETECTION OF COMPRESSIVE RESIDUAL STRESSES USING THE METHOD OF CAUSTICS

[75] Inventors: Basil P. Leftheris, Huntington; Robert C. Schwarz, Dix Hills, both of N.Y.

[73] Assignee: Grumman Aerospace Corporation, Bethpage, N.Y.

[21] Appl. No.: 352,305

[22] Filed: May 16, 1989

[51] Int. Cl.$^5$ ............................................. G01B 11/16
[52] U.S. Cl. ........................................ 356/32; 73/800
[58] Field of Search ....................... 356/32, 33, 34, 35; 73/799, 800, 802

[56] References Cited

U.S. PATENT DOCUMENTS

| | | | |
|---|---|---|---|
| 3,854,325 | 12/1974 | Coate . | |
| 4,119,380 | 10/1978 | Raftopoulos et al. | 356/32 |
| 4,195,929 | 4/1980 | Raftopoulos et al. | 356/32 |
| 4,255,049 | 3/1981 | Sahm et al. | 356/32 |
| 4,547,073 | 10/1985 | Kugimiya | 356/371 |

OTHER PUBLICATIONS

"Plane Surface Strain Examination by Speckle-Pattern Interferometry Using Electronic Processing", Journal of Strain Analysis, vol. 9, No. 1, Jan. 1974, pp. 17-25.
"Speckle-Shearing Interferometric Technique: A Full-Field Strain Gauge", Applied Optics, vol. 14, No. 3, Mar. 1975, pp. 618-622.
"Application of the Method of Caustics to the Determination of the Ratio of Poisson's Ratio to the Modulus of Elasticity", J. Phys. D: Applied Physics, vol. 12, No. 8, Aug. 1979, pp. 1321-1324.

Primary Examiner—F. L. Evans
Attorney, Agent, or Firm—Pollock, VandeSande & Priddy

[57] ABSTRACT

The method of caustics employs a laser for illuminating an extended crack in stock sheet metallic material. A shadow area image is generated which has geometrical parameters which may be measured and applied to the calculation of stress intensity factor ($K_I$). The variation of the shadow shape in response to specimen loading provides signatures corresponding with the degree and direction of residual stresses in the material adjacent a hole formed in the material. By determining stress-intensity factors and stress-intensity distributions, a higher degree of quality control for sheet stock material becomes possible in addition to allowing the assembling of such material in directions that will best counteract anticipated destructive external forces.

6 Claims, 1 Drawing Sheet

DETECTION OF COMPRESSIVE RESIDUAL STRESSES USING THE METHOD OF CAUSTICS

FIELD OF THE INVENTION

The present invention relates to a photographic technique for inspecting metal materials, and more particularly to such a method employing the method of caustics.

BACKGROUND OF THE INVENTION

Crack-growth information is important in estimating fatigue life in metallic structures, such as employed in aircraft fabrication. With respect to the latter-mentioned structures, the interaction between existing residual stresses in aluminum alloy sheet stock and residual stresses induced by cold working holes is difficult to evaluate analytically, mainly because existing residual stresses are not clearly defined. Accordingly, there is a need to experimentally evaluate fatigue specimens under cyclic loading so that critical fatigue life parameters, such as intensity factor $K_I$ can be determined during crack growth. This would better enable inspectors to determine whether supplied stock sheet material has been properly manufactured and, in the event holes are formed in such material and cold worked, the success of such cold working can be determined The method of "caustics" or shadow photography has been used in recent years for the evaluation of strain fields near crack tips in laboratory work. These methods have generally been used in connection with brittle materials which develop short cracks after cyclic loading and then quickly fail. Data evaluation of crack tips in such material have been analyzed by investigators. To date, there has been no known attempted use of this method for the evaluation of residual stresses around holes formed in more ductile sheet materials where cracks can form along a fairly long length before structural failure. In a number of industries, such as the aircraft fabrication industries, the fatigue life before such structural failure is of obvious great concern.

BRIEF DESCRIPTION OF THE INVENTION

The present invention is directed to the evaluation of residual stresses around holes formed in ductile sheet material. Rather than photographically investigating only a crack tip, the present invention extends the prior art so that residual stresses around holes are determined by using a beam in a global sense, covering an area several hundred times larger than that for a crack tip. When an elongated crack becomes present, this area includes the tail of the crack. By employing the method of caustics, a dark strip or "caustic tail" may be observed. When a specimen with a crack is statically loaded, the caustic tail changes in thickness. The caustic pattern around the hole surrounded by a uniform stress field will change from circular to oblong upon the application of tension during fatigue testing, thereby permitting real time observation of variations in the residual stress and permitting at least a rough calibration of the residual stress levels. By measuring certain caustic geometry, the method of the present invention enables an investigator or inspector to evaluate crack closure stresses and stress-intensity factors during cyclic loading The method of caustics, also known as the shadow method, can be used during cyclic fatigue testing, without interrupting the test, to evaluate the stress-intensity factors in longitudinal and long transverse directions. Specimens with both open holes and with cold worked holes may be tested.

In terms of useful applications in the aircraft industry, the present invention may be employed to evaluate sheet stock material used in aircraft structures. Further, sheet stock material may be investigated to determine whether initial residual stresses, after manufacture, are sufficient to produce adequate fatigue life enhancement without additional cold working.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

During the generation of a crack in metallic sheet materials there is an interaction of compressive force effects during fatigue loading. The interaction effects, or crack closure, is the result of plastic deformation of the material during crack growth. The more ductile the material, the greater the compressive force along the crack surface. Geometry (i.e., edge crack, cracks originating from fastener holes) and residual stresses from stress relief methods (i.e., stretching) also influence closure. The method of caustics has been used in the evaluation of stress-intensity factor $(K_I)$ at a crack tip during dynamic loading. The basis of the present invention is the expansion of the method of caustics in recognition of the fact that this method may be employed to include investigation of an entire crack length. This enables the present invention to be employed in the evaluation of the radius of plasticity $r_{yd}$, and the residual stress that causes crack closure in sheet materials such as aluminum alloys.

In order to employ the method of caustics, it is necessary to set up a photographic system which will generate shadow photographs of a crack in a metal material.

Figure 1:
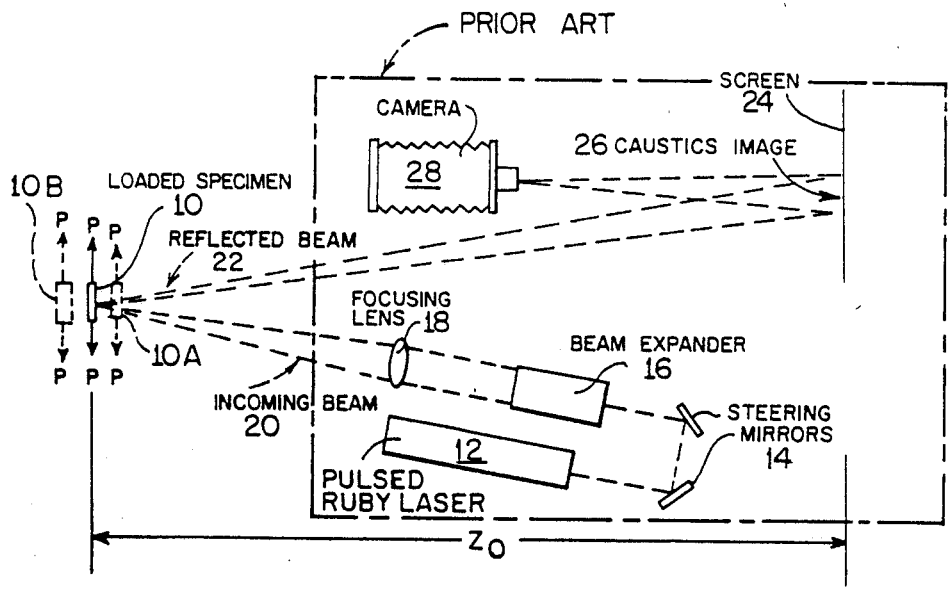
FIG. 1 is a diagrammatic representation of a laser-optics system for generating caustics.

FIG. 1 illustrates a ruby laser system for recording caustics during crack growth. The apparatus disclosed is conventionally used in investigating crack tip caustics of a loaded specimen 10, which is typically a sheet of stock alloy material, such as aluminum. The caustics are promulgated by a pulsed ruby laser 12 which generates a beam that becomes steered by mirrors 14 toward the loaded specimen 10 after passing through a beam expander 16 and focusing lens 18. In the prior art discussed, where only crack tips have been the incoming beam 20 has its focal point behind the plane of the surface of the loaded specimen 10. The specimen 10 ordinarily undergoes dynamic loading to generate a crack of reasonable length necessary to conduct an analysis thereon. Thereafter, the loading on specimen 10 may continue to be dynamic or static, depending upon the observations desired by an investigator.

A beam 22 is reflected from the specimen 10 and impinges upon a screen 24 so that a caustic image 26 is displayed. An adjacent camera 28 is directed toward the image 26 and the camera 28 is synchronized to the pulsing of ruby laser 12 and the application of dynamic loading on specimen 10. If static loading is applied, a continuous laser beam may be employed.

In the present invention, it has been determined from an apparatus point of view that, when investigating the compressive residual stresses in manufactured stock sheet material (non-cold worked), a loaded specimen is positioned so that the focal point of incoming beam 20 falls immediately behind the surface of the loaded specimen, as indicated by the specimen 10A appearing in dotted lines. If, on the other hand, a cold worked area, such as around a prepared rivet hole, is to be investigated, the loaded specimen 10 is to be moved so that the focal point of the incoming beam 20 falls in front of the surface as indicated by the specimen 10B shown in dotted lines. This displacement of the focal point away from the plane of the specimen will create a larger caustic area corresponding to the entire crack length, as opposed to only the crack tip which was the limitation of the prior art.

Pictures of caustics taken with the set-up of FIG. 1 but with the specimens being displaced from the focal point (10A, 10B) are taken during dynamic loading and at peak load points by synchronizing the laser with the camera and a conventional load cell (not shown) that controls the load. The transverse diameter of the caustic ($D_t$) may then be measured on the photograph taken of the caustics and $K_I$ is evaluated using the equation $$K_I = \frac{2\sqrt{2\pi}}{3v\lambda C t Z_o} \left(\frac{D_t}{3.17}\right)^{\frac{5}{2}}$$

where lambda is the magnification factor and $Z_o$ is the distance between the specimen and screen as shown in FIG. 1. The transverse diameter of the caustic ($D_t$) is then measured and the dynamic stress intensity factor of Mode I ($K_I$) is evaluated using known equations that relate these two quantities for isotropic materials.

Figure 2:
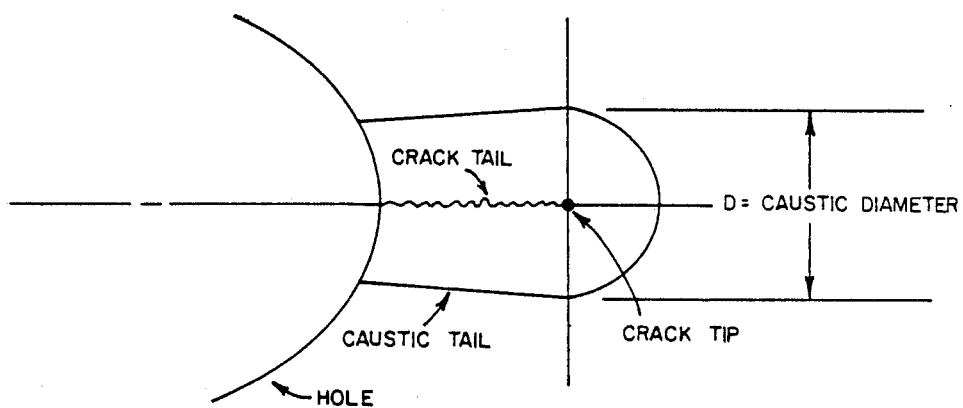
FIG. 2 is a diagrammatic illustration of a caustic image.

FIG. 2 schematically illustrates the profile for a crack extending radially outwardly from a hole formed in a metal sheet material. The indicated crack tail represents the actual physical crack, while the caustic tail represents a shadow area boundary which may be thought of as a residual stress signature for a particular crack. As is clearly indicated in FIG. 2, the caustic tail area extends well beyond the actual crack tail and crack tip. The signature of the caustic tail will vary depending upon the residual stress in the material adjacent the hole. The signature will also vary for a particular material sheet depending upon whether the hole has been cold worked or not. Accordingly, after a crack tail has been grown to a certain length, the signature of a caustic tail in the area of a hole may be investigated to determine the residual stress interactions which relate to fatigue life in a manner well known to those having ordinary skill in the metallurgical arts.

The method of caustics can be used to evaluate crack closure. First, one can find the closure pressure which is the superposition of plastic deformation along the crack and residual stresses locked in during material fabrication of a metal sheet, such as aluminum. Second, by applying a static load to a cracked specimen, one can evaluate the history of loading of the crack near the hole. For example, when the caustic tail closes as the remote static load increases, the direction of the residual stresses is in the direction of the applied load. By comparison, when the width of the caustic tail remains unchanged, the residual stress is perpendicular to the load direction.

The method of caustics may be handily employed in the evaluation of crack closure in cold worked holes. It is well known that, when fastener holes in certain metallic structures, such as in aircraft, are cold worked, the resulting residual compressive stresses reduce crack growth rates and thus enhance fatigue life. Fatigue enhancement by cold working holes is the result of the residual compressive stresses (both radial and circumferential). If initial residual stresses exist, the resultant residual field will reflect their existence.

In order to determine whether cold working a hole in a particular material sheet has enhanced the fatigue characteristics of the hole, the method of caustics may be employed to investigate the caustic tail while the static load changes. If there is no meaningful change in a broad region of static load increases, this is an indication of no fatigue enhancement.

From the above description of the invention, it will be seen that the caustics method of crack shadow analysis is an efficient way to evaluate the stress intensity factor $K_I$ in specimens undergoing fatigue testing. The accuracy of this method affords one the opportunity to conduct diagnostic work during crack growth in complex stress fields. Since analysis of cracks with the caustics method shows that the fatigue loading in the longitudinal and transverse directions produce extensive differences in both crack growth rates and fatigue behavior. The present invention enables a manufacturer to orient sheet material in a direction wherein residual stresses will oppose anticipated externally imposed loads so as to increase the useful life of an assembled structure. Accordingly, application of the present invention is useful, not only as a quality control or inspection tool, but also for maximizing the advantages of initial residual stresses in sheet stock material so as to obtain fatigue life enhancement without additional cold work.

It should be understood that the invention is not limited to the exact details of construction shown and described herein for obvious modifications will occur to persons skilled in the art.

We claim:

1. A method for detecting the residual stress around a hole formed in a metal sheet specimen, the method comprising the steps of:
    loading the specimen with a preselected force;
    directing an incoming laser beam toward the hole in the specimen at a focal point aligned with the hole and immediately outside the specimen;
    directing a beam reflected from the specimen toward a screen so that a caustic image is displayed thereon; and
    photographing the resulting caustic image on the screen, the image including a caustic tail related in length to a crack tail extending between the hole and a crack tip, in a generally radially outward direction;
    wherein the geometry of the image is indicative of the residual stress in the vicinity of the hole.

2. The method set forth in claim 1 wherein the hole is initially cold worked and the focal point is in front of the specimen surface confronting the incoming beam.

3. The structure set forth in claim 1 wherein the hole is not initially cold worked and the focal point is behind the specimen relative to the incoming beam.

4. A method for detecting the residual stress around a hole formed in a metal sheet specimen, the method comprising the steps of:
- cyclically loading specimen of alloy sheet stock having a hole formed therein resulting in crack growth outside the hole;
- directing an incoming laser beam toward the hole in the specimen at a moment of maximum force application, at a focal point aligned with the hole and immediately outside the specimen;
- directing a beam reflected from the specimen toward a screen so that a caustic image is displaced thereon; and
- photographing the resulting caustic image on the screen, the image including a caustic tail related in length to a crack tail extending between the hole and a crack tip, in a generally radially outward direction;
- wherein the geometry of the image is indicative of the residual stress in the vicinity of the hole.

5. The method set forth in claim 4 wherein the hole is initially cold worked and the focal point is in front of the specimen surface confronting the incoming beam.

6. The method set forth in claim 4 wherein the hole is not initially cold worked and the focal point is behind the specimen relative to the incoming beam.

* * * * *

UNITED STATES PATENT AND TRADEMARK OFFICE
CERTIFICATE OF CORRECTION

PATENT NO.   :   4,953,973
DATED        :   September 4, 1990
INVENTOR(S)  :   Basil P. Leftheris, et al.

It is certified that error appears in the above-identified patent and that said Letters Patent is hereby corrected as shown below:

Column 1, line 65, after "ing" insert --.--.

Column 2, line 56, after "have been" insert --investigated--.

Column 5, line 4, after "loading" insert --a--.

Signed and Sealed this

Seventh Day of January, 1992

*Attest:*

HARRY F. MANBECK, JR.

*Attesting Officer*   *Commissioner of Patents and Trademarks*